United States Patent [19]

Liebman et al.

[11] 4,150,042
[45] Apr. 17, 1979

[54] 6-HYDROXY-7-METHOXY-5-BENZOFURAN CARBOXALDEHYDE AND 2,3-DIHYDRO-7-METHOXY-6-BENZOFURANOL

[75] Inventors: Arnold A. Liebman, Verona; Yu-Ying Liu, Westwood, both of N.J.

[73] Assignee: Hoffmann-La Roche Inc., Nutley, N.J.

[21] Appl. No.: 884,784

[22] Filed: Mar. 8, 1978

Related U.S. Application Data

[62] Division of Ser. No. 820,265, Jul. 29, 1977, Pat. No. 4,107,182.

[51] Int. Cl.$^2$ .......................................... C07D 307/86
[52] U.S. Cl. ................................................. 260/346.22
[58] Field of Search ..................................... 260/346.22

[56] References Cited

U.S. PATENT DOCUMENTS

| | | | |
|---|---|---|---|
| 2,659,734 | 11/1953 | Geissman | 260/346.22 |
| 3,470,165 | 9/1969 | Fitzmaurice | 260/346.22 |

*Primary Examiner*—Natalie Trousof
*Assistant Examiner*—Bernard Dentz
*Attorney, Agent, or Firm*—Jon S. Saxe; Bernard S. Leon; Frank P. Hoffman

[57] ABSTRACT

The invention relates to synthetic processes to produce the known pharmacologically active 9-methoxypsoralen. Also disclosed are various novel intermediates utilized in these processes.

2 Claims, No Drawings

6-HYDROXY-7-METHOXY-5-BENZOFURAN CARBOXALDEHYDE AND 2,3-DIHYDRO-7-METHOXY-6-BENZOFURANOL

This is a division, of application Ser. No. 820,265 filed July 29, 1977, now U.S. Pat. No. 4,107,182.

BACKGROUND OF THE INVENTION

It is known that either the topical application or oral ingestion of certain chemical compounds, known as furocoumarins, certain isomers of which are called psoralens, have an effect on the responsiveness of human skin to sunlight. These psoralen compounds, including 9-methoxypsoralen, which has the generic name of methoxsalen, have long been used in the treatment of certain skin diseases, such as vitiligo, which is characterized by a spotty loss of pigmentation of the skin.

The compound 9-methoxypsoralen having the structural formula

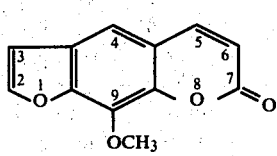

and the chemical name 9-methoxy-7H-furo[3,2-g][1]benzopyran-7-one has been obtained from natural sources, namely from the fruit of the Ammi Majus Linn. plant, see for example, Fabmu et al., "Ammi Majus Linn. Pharmacognostical study and isolation of crystalline constituent, Ammoidin", Quart. J. Pharm. and Pharmacol., 21:449, 1948.

The present invention is drawn to synthetic processes to produce the compound 9-methoxypsoralen. The following reaction scheme represents the various process steps and novel intermediates which may be utilized to produce methoxsalen (compound of formula I).

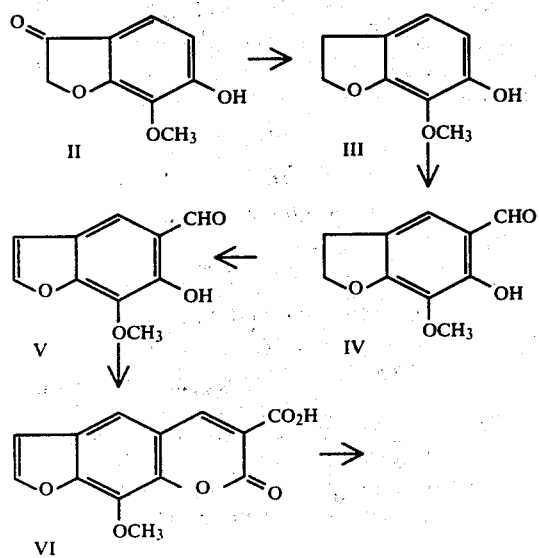

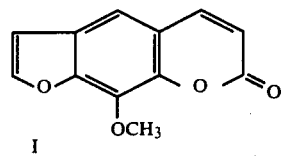

II→III

The benzofuranone of the formula II was prepared from 2,6-dihydroxyanisole following procedures set forth by Geissman et al. in Journal of the American Chemical Society, Vol. 73, 5765 (1951). Thereafter the compound of formula II is hydrogenated utilizing hydrogen and a Noble metal such as Palladium on carbon or Platinum in a solvent such as acetic acid. The reaction is carried out at a temperature range of about 15° C. to 50° C. with room temperature preferred. The reaction may be run at atmospheric pressure or under pressures of up to 10 atmospheres with three (3) atmospheres as preferred.

III→IV

The compound of formula III is thereafter reacted (Gattermann reaction) with zinc cyanide and hydrochloric acid at about room temperature to provide a compound of formula IV.

IV→V

The compound of formula IV is thereafter dehydrogenated utilizing dichlorodicyanoquinone in an inert solvent such as dioxane, cyclic ethers such as tetrahydrofuran, or benzene from reflux temperature for the mixture to room temperature with reflux temperature as preferred.

V→VI

The compound of formula V is thereafter reacted with ethyl cyanoacetate to provide the condensed product of formula VI. The reaction is preferably carried out in polar solvent, such as, water and at room temperature.

VI→I

The compound of formula VI is thereafter decarboxylated by heating e.g., above 200° C. in the presence of calcium carbonate.

Yet another variation of the above process sequence involves the following reaction scheme:

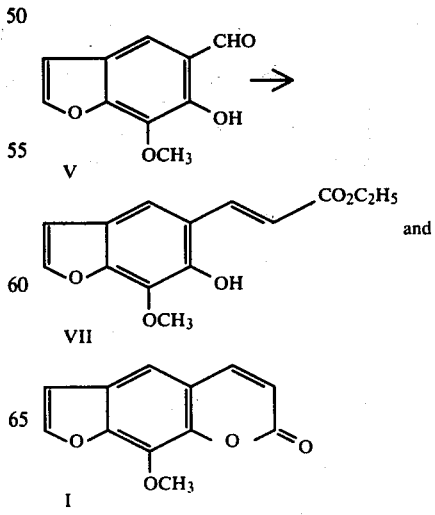

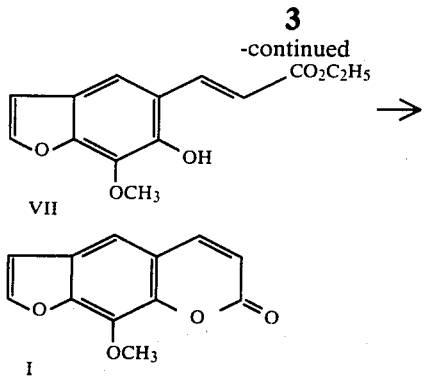

VII

I

V→VII and I

The compound of formula V is reacted with phosphorane of the formula $Ph_3P=CHCO_2C_2H_5$ in a Wittig condensation reaction to form the mixture of compounds VII and I. The reaction is carried out in a polar or non-polar inert organic solvent such as methanol, tetrahydrofuran, dioxane, aromatic hydrocarbons such as benzene, high boiling ethers and dimethyl sulfoxide. The reaction temperature ranged from room temperature to reflux, with reflux temperature as preferred.

VII→I

The open compound of formula VII is converted to the closed end product by heating of the open compound under nitrogen, i.e., at a temperature of about 200° C. for at least 30 hours or by photoconversion utilizing methods well known in the art.

It should be noted that intermediate compounds of the formulas III, V, VI and VII are new compounds and as such form a part of the invention since they lead to the useful end product "methoxsalen".

The invention is further illustrated by the following examples. Unless otherwise indicated, all temperatures given are in degrees centigrade.

EXAMPLE 1

α-Chloro-2,4-dihydroxy-3-methoxyacetophenone

From 19.6 g. (0.14 mole) of 2,6-dihydroxyanisole, 10.7 g. (0.14 mole) of chloroacetonitrile and 10 g. of freshly fused zinc chloride, the crude product, isolated as described in the T. A. Geissman and W. Moje article, J. Amer. Chem. Soc., 73, 5765 (1951), was purified by chromatography over silica gel (E. Merck 60), eluting with chloroform followed by crystallization from water-methanol to yield a colorless solid, m.p. 71°–72°.

EXAMPLE 2

6-Hydroxy-7-methoxy-3(2H)-benzofuranone

As described in the Geissman et al. article referenced in Example 1, 23.4 g. (0.108 mole) of α-chloro-2,4-dihydroxy-3-methoxyacetophenone was treated with a solution of 29 g. of anhydrous sodium acetate in 80 ml. of absolute ethanol. After recrystallization from methanol, the end product was isolated as a colorless solid, m.p. 160°.

EXAMPLE 3

2,3-Dihydro-7-methoxy-6-benzofuranol

A solution of 6-hydroxy-7-methoxy-3(2H)-benzofuranone, 233 mg. (1.29 mmole) in 5 ml. of acetic acid was hydrogenated for 4 hours at room temperature under 53 psi of $H_2$ using 50 mg. of 10% Pd/C as catalyst. The mixture was then filtered, concentrated in vacuo to a residue which was chromatographed over silica gel (E. Merck 60) eluting with $CHCl_3$ to yield, after evaporation, a colorless oil.

EXAMPLE 4

2,3-Dihydro-6-hydroxy-7-methoxy-5-benzofurancarboxaldehyde

A mixture of 2.49 g. (15 mmole) of 2,3-dihydro-7-methoxy-6-benzofuranol, 5.87 g. (50 mmole) zinc cyanide and 100 ml. of dry ether was saturated with hydrogen chloride for 1 hour at 0°, then for 2 hours at room temperature. The mixture was then allowed to stand overnight at room temperature then concentrated in vacuo and the residue treated with 100 ml. of 0.1N HCl for 1 hour at reflux. After cooling, ether extraction provided the product which was purified by chromatography over silica gel (E. Merck 60), eluting with $CHCl_3$, to yield a colorless solid, m.p. 71°–72°.

EXAMPLE 5

6-Hydroxy-7-methoxy-5-benzofurancarboxaldehyde

A solution of 817 mg. (3.6 mmole) of DDQ in 10 ml. of dioxane was added to 582 mg. (3 mmole) of 2,3-dihydro-6-hydroxy-7-methoxy-5-benzofuran-carboxaldehyde in 15 ml. of dioxane and the resulting mixture was heated under reflux for 7 hours, cooled and the formed solid removed by filtration. The precipitate was thoroughly washed first with benzene, then with $CHCl_3$. The washings were combined with the initial filtrate and the total concentrated in vacuo to a residue which was chromatographed first on a 20 ml. dry silica gel column (E. Merck 7734) with $CHCl_3$ elution followed by conventional chromatography over 20 g. of silica (E. Merck 7734) packed in benzene-ethyl acetate (95:5) and elution with this solvent mixture provided, after workup, a yellow solid, m.p. 60°–62°.

EXAMPLE 6

7-Oxo-9-methoxy-7H-furo[3,2-g][1]benzopyran-6-carboxylic acid

The aldehyde of Example 5 (192 mg., 1 mmole) in 1 ml. of water was added to a solution of ethyl cyanoacetate (125 mg., 1.1 mmole) in 1 ml. of water containing 200 mg. of sodium hydroxide. The mixture was stirred at room temperature for 20 hours then treated with 8 ml. of 2N HCl under reflux for 30 minutes. After cooling, the product was isolated by centrifugation followed by crystallization from ethanol to yield a yellow solid, m.p. 227°–228°.

EXAMPLE 7

6-Hydroxy-7-methoxy-benzofuran-5-trans-acrylic acid ethyl ester

A mixture of the aldehyde of Example 5 (192 mg., 1 mmole) and carbethoxymethylenetriphenylphosphorane, 666 mg., 1.9 mmole [prepared from triphenylphosphine and ethyl bromoacetate as described in the article by B. Denny and S. T. Ross, J. Org. Chem., 27, 998 (1962)] in 20 ml. of benzene was heated under reflux for 2 hours. The solvent was removed by distillation in vacuo and the residue was chromatographed over silica gel (E. Merck 60) with benzene to provide a colorless solid, m.p. 127°–128°.

EXAMPLE 8

9-Methoxyfuro[3,2-g]coumarin(9-Methoxypsoralen or Methoxsalen)

A. A 240 mg. (0.923 mmole) sample of 7-oxo-9-methoxy-7H-furo[3,2-g][1]benzopyran-6-carboxylic acid was intimately mixed with 300 mg. of CaCO₃ and the mixture was heated under N₂ at 210° for 45 minutes. After cooling, the mixture was slurried with CHCl₃, filtered and the filtrate concentrated in vacuo to a residue which was chromatographed over silica gel (E. Merck 60) with benzene elution to yield a colorless solid, m.p. 146°–148° and identical to authentic methoxsalen by tlc (5% ethyl acetate in benzene elution).

B. A 216 mg. (0.83 mmole) sample of 6-hydroxy-7-methoxybenzofuran-5-transacrylic acid ethyl ester was heated, under N₂, to 200° and held at that temperature for 30 hours. The resulting material was dissolved in benzene and chromatographed over silica gel (E. Merck 60) with benzene elution thereby providing methoxsalen, again identical to authentic methoxsalen.

What is claimed:

1. A compound of the formula

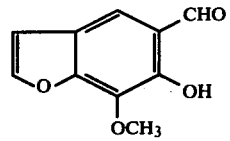

2. A compound of the formula

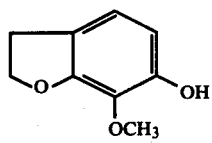

* * * * *